United States Patent [19]

Bach et al.

[11] Patent Number: 4,600,534

[45] Date of Patent: Jul. 15, 1986

[54] PROCESS AND INTERMEDIATES FOR MANUFACTURE OF 3-(5-AMINO-1-CARBOXYPENTYLAMINO)-TETRAHYDRO-1-BENZAZEPIN-2-ONE-1-ACETIC ACID

[75] Inventors: Joseph Bach, Parsippany; Stephen K. Boyer, Far Hills, both of N.J.

[73] Assignee: Ciba-Geigy Corporation, Ardsley, N.Y.

[21] Appl. No.: 662,313

[22] Filed: Oct. 18, 1984

[30] Foreign Application Priority Data

Feb. 6, 1984 [EP] European Pat. Off. ........ 84810072.3

[51] Int. Cl.⁴ .................. C07D 223/16; C07D 401/12
[52] U.S. Cl. .............................................. 260/239.3 B
[58] Field of Search ................................... 260/239.3 B

[56] References Cited

U.S. PATENT DOCUMENTS 4,473,575  9/1984  Watthey ........................ 260/239.3 B

FOREIGN PATENT DOCUMENTS 107095  5/1984  European Pat. Off. ..... 260/239.3 B
119954  9/1984  European Pat. Off. ..... 260/239.3 B
119955  9/1984  European Pat. Off. ..... 260/239.3 B

*Primary Examiner*—Robert T. Bond
*Attorney, Agent, or Firm*—Norbert Gruenfeld

[57] ABSTRACT

The invention concerns a novel process for the preparation of 3-(5-amino-1-carboxypentylamino)-tetrahydro-1-benzazepin-2-one-1-acetic acid by opening, preferably under acidic conditions, the caprolactam ring in a compound of formula II

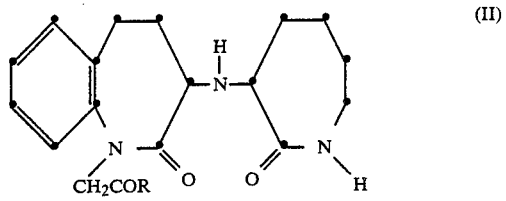

(II)

wherein COR represents carboxy or esterified carboxy, and hydrolyzing the esterified carboxy group if present. The preparation of the starting materials of formula II is described.

16 Claims, No Drawings

PROCESS AND INTERMEDIATES FOR MANUFACTURE OF 3-(5-AMINO-1-CARBOXYPENTYLAMINO)-TETRAHYDRO-1-BENZAZEPIN-2-ONE-1-ACETIC ACID

SUMMARY OF THE INVENTION

The present invention concerns an unexpectedly useful novel process for the preparation of 3-(5-amino-1-carboxypentylamino)-tetrahydro-1-benzazepin-2-one-1-acetic acid of formula I

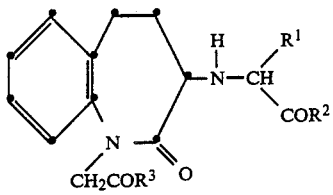

wherein $R^1$ represents 4-aminobutyl, $COR^2$ and $COR^3$ represent carboxy; and pharmaceutically acceptable salts thereof, disclosed as selective inhibitors of angiotensin-converting enzyme in mammals for the treatment of hypertension and cardiac conditions, e.g. in commonly owned U.S. application Ser. No. 465,695, now U.S. Pat. No. 4,473,575, which is incorporated herein by reference.

The process relates to the use of a novel lactam of formula II as reactant and starting material for the preparation of a compound of formula I.

The instant process involves the surprising selective opening of the monocyclic lactam, i.e. the caprolactam ring, in a compound of formula II

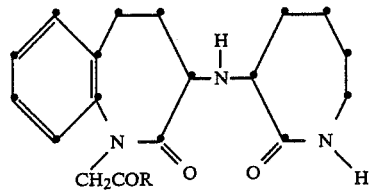

wherein COR represents carboxy or esterified carboxy, and hydrolysis of the esterified carboxy group if present, to yield an amino acid of formula I; and if desired, a resulting compound of formula I is converted into a salt thereof, or a resulting salt into another salt, or a free compound is liberated from such a salt; and if so required, an isomer of formula I which has a specific configuration with respect to the two centers of chirality is separated from a resulting mixture of stereoisomeric forms.

The invention also relates to novel starting materials of formula II and processes for their manufacture.

The compounds of formula I have two asymmetric carbon atoms and can exist in the form of four stereoisomers comprising two racemic diastereoisomers each consisting of two optically active antipodes.

DETAILED DISCLOSURE OF THE INVENTION

More specifically the process concerns a new process for the preparation of the preferred isomer, 3-[(5-amino-1-carboxy)-(1S)-pentylamino]-1-carboxymethyl-2,3,4,5-tetrahydro-1H-1(3S)-benzazepin-2-one of formula Ia

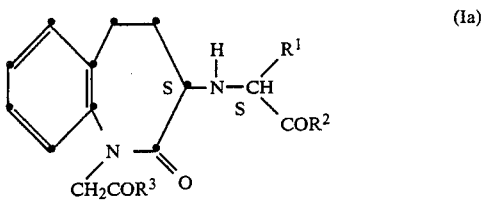

wherein $R^1$ represents 4-aminobutyl, $COR^2$ and $COR^3$ represent carboxy, and S represents the chirality; and pharmaceutically acceptable salts thereof.

Pharmaceutically acceptable salts are preferably mono- or di- metal or ammonium salts of said compounds of formula I or Ia, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)amines, lower alkylenediamines or (lower hydroxyalkyl or aralkyl)alkylammonium bases, e.g., methylamine, diethylamine, triethylamine, dicyclohexylamine, triethanolamine, ethylenediamine, tris-(hydroxymethyl)aminomethane or benzyltrimethylammonium hydroxide. Said compounds of formula I form mono- or di- acid addition salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid. Preferred are the mono or dihydrochloride salts.

The novel process of this invention for the manufacture of the preferred compound of formula Ia comprises the selective ring opening the monocyclic lactam in a compound of formula IIa

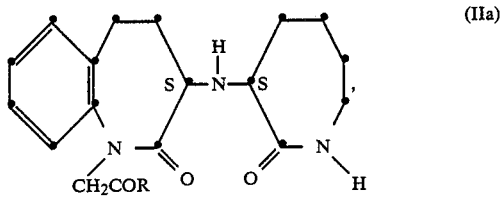

or a mixture of stereoisomers containing said compound, wherein COR represents carboxy or esterified carboxy, to the compound of formula Ia; and if desired, the resulting compound of formula Ia is converted into a salt thereof or a resulting salt into another salt, or the free compound is liberated from such a salt, and if so required, the optical isomer of formula Ia which has the specific S,S configuration with respect to the two centers of chirality is separated from a resulting mixture of stereoisomeric forms.

The process of the instant invention is preferably carried out under acidic conditions.

The general definitions used herein have the following meanings within the scope of the present invention.

Esterified carboxy represents preferably lower alkoxycarbonyl, benzyloxycarbonyl, benzyloxycarbonyl substituted in the phenyl ring by lower alkyl, halogen or lower alkoxy, e.g. methyl, chloro or methoxy respectively, or pyridylmethoxycarbonyl.

The term "lower" referred to above and hereinafter in connection with organic radicals or compounds respectively defines such with up to and including 7, preferably up and including 4 and advantageously one or two carbon atoms.

A lower alkyl group contains 1-7 carbon atoms, preferably 1-4 carbon atoms and represents for example ethyl, propyl, butyl or advantageously methyl.

A lower alkoxy group preferably contains 1-4 carbon atoms and represents for example methoxy, propoxy, isopropoxy or advantageously ethoxy.

Halogen preferably represents chlorine, but may also be bromine, fluorine or iodine.

Lower alkoxycarbonyl represents preferably $C_1$-$C_4$-alkoxycarbonyl, advantageously methoxycarbonyl, ethoxycarbonyl or t-butoxycarbonyl.

According to the process of this invention, the opening of the monocyclic caprolactam ring is carried out by treatment with preferably a strong aqueous acid preferably at an elevated temperature, e.g. ranging between about 50° and 150° C., optionally in the presence of a polar organic solvent such as tetrahydrofuran or dioxane or any other commonly used water-miscible inert solvent. Suitable acids include mineral acids, for example hydro-halic, e.g. hydrocloric or hydrobromic acid; sulfuric, phosphoric; lower alkylcarboxylic acids, such as trifluoro-acetic acid; lower alkylsulfonic acids such as methane- sulfonic acid or trifluoromethanesulfonic acid; an acidic ion exchange resin, e.g. a strongly acidic cation exchange resin with e.g. a sulfonic acid functionality.

Preferred is hydrochloric acid at a concentration ranging from 2N to 10N, advantageously 6N to 10N, at a temperature of about 80°-110° C.

In a compound of formula II wherein $COR^3$ represents esterified carboxy, said ester is first or simultaneously converted to free carboxy under the reaction conditions described above.

Surprisingly, the opening of the monocyclic hexahydro-2H-azepin-2-one ring (the caprolactam ring) is achieved without significant opening of the other lactam in the bicylic tetrahydro-1H-[1]-benzazepin-2-one portion of the compounds of formula II.

The reactants of formula II are preferably prepared by (a) reductive N-alkylation of 3-aminocaprolactam with a compound of formula III

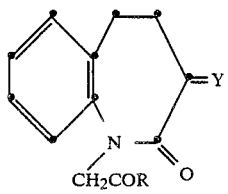

(III)

wherein Y is oxo, and COR represents carboxy or esterified carboxy; or (b) N-alkylation of 3-aminocaprolactam with a compound of formula III wherein COR has meaning as defined above and Y represents one reactive esterified hydroxy group together with hydrogen.

For the preparation of the S,S-compound of formula IIa, 3-(S)-aminocaprolactam is preferably used as starting material.

A reactive esterified hydroxyl group is such as a hydroxyl group esterified with a strong organic acid, e.g. an aliphatic or aromatic sulfonic acid (such as a lower alkanesulfonic acid, especially methanesulfonic, trifluoromethanesulfonic acid, or an arylsulfonic acid especially benzenesulfonic, p-toluenesulfonic, p-bromobenzenesulfonic and p-nitrobenzenesulfonic acid) or with a stronginorganic acid, such as, especially sulfuric acid or a hydrohalic acid, such as hydrochloric, hydriodic or hydrobromic acid. Preferrred as the esterified hydroxyl group is halo, advantageously chloro or bromo.

N-Alkylation by direct substitution is carried out under conventional general conditions at temperatures ranging between about 0° C. up to the boiling temperature of the reaction mixture, preferably at temperatures between room temperature and about 100° C. The reaction takes place advantageously in the presence of a solvent which is inert with respect to the reactants, such as acetonitrile, a chlorinated lower alkane (e.g. chloroform or methylene chloride), an acyclic or cyclic ether (e.g. diethyl ether, 1,2-dimethoxyethane, dioxane or tetrahydrofuran), or a lower molecular weight tertiary amide (e.g. N,N-dimethylformamide, N,N-dimethylacetamide, N-methylpyrrolidone, N-ethylpiperidone and hexamethylphosphoric acid triamide). Advantageously, the strong acid liberated during the reaction is bound by the addition of an acid-binding agent, such as, preferably, an inorganic acid-scavenger such as an alkali metal bicarbonate, carbonate or hydroxide, an organic quaternary ammonium salt (e.g. a tetrabutylammonium salt) or an organic tertiary base, such as triethylamine, N-ethylpiperidine, pyridine or quinoline.

Reductive alkylation by condensation of 3-aminocaprolactam with the compound of formula III wherein Y is oxo and COR is carboxy or esterified carboxy is carried out under conditions generally known and used in the art, e.g. by catalytic hydrogenation with hydrogen in the presence of a catalyst such as palladium or Raney nickel, or by reaction in the presence of a chemical reducing agent, advantageously an alkali metal cyanoborohydride such as sodium cyanoborohydride. The reductive alkylation with an alkali metal cyanoborohydride is preferably carried out in an inert solvent, e.g. methanol or acetonirile, advantageously in the presence of an acid, e.g. hydrochloric acid or acetic acid.

The starting materials of formula III can be prepared according to methods described in U.S. Pat. No. 4,410,520 and U.S. patent application Ser. No. 465,695, now U.S. Pat. No. 4,473,575, which are incorporated herein by reference, and as described in the examples herein.

For example, the preparation of 3-bromo-1-ethoxycarbonylmethyl-2,3,4,5-tetrahydro-1H-[1]-benzazepin-2-one is described in example 31 of U.S. Pat. No. 4,410,520 and the preparation of 1-ethoxycarbonylmethyl-2,3,4,5-tetrahydro-1H-[1]-benzazepin-2,3-dione is described in Example 40 of U.S. patent application Ser. No. 465,695, now U.S. Pat. No. 4,473,875.

The compounds of formula II form acid addition salts, and metal or ammonium salts when COR represents carboxy. Acceptable salts are preferably pharmaceutically acceptable salts as described above for the compounds of formula I and formula Ia.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Whenever desirable, the above processes are carried out after first suitably protecting any potentially interfering reactive functional groups by methods generally known in the art.

Advantageously, those starting materials should be used in said reactions that lead to the formation of those compounds indicated above as being preferred.

Depending on the choice of starting materials and methods, the new compounds may be in the form of one of the possible isomers or mixtures thereof, for example, as pure diastereoisomers, as pure optical isomers (as antipodes), or as mixtures of optical isomers, i.e. as racemates.

In case the diastereomeric mixtures of the above compounds or intermediates are obtained, these can be separated into the single racemic or optically active isomers by methods in themselves known, e.g. by fractional distillation, crystallization and/or chromatography.

For example, when 3-(S)-aminocaprolactam is used as the starting material in the above processes, the (S,S)-diastereoisomer of formula IIa is isolated from the resulting mixture of the (S,S) and (R,S)-diastereoisomers by crystallization from an appropriate inert solvent, e.g. a lower alkanol such as methanol.

The racemic diastereoisomers of formula I and the intermediates of formula II can be resolved into the optical antipodes, for example, by separation of diastereomeric salts thereof, e.g., by the fractional crystallization of d- or l-(tartrate, dibenzoyltartrate, mandelate or camphorsulfonate) salts.

The racemic products of formula I or the racemic acidic intermediates of formula II can also be resolved by separation of e.g. the d- or l-($\alpha$-methylbenzylamine, cinchonidine, cinchonine, quinine, quinidine, ephedrine, dehydroabietylamine, brucine or strychnine)salts of such compounds having an acidic salt-forming group.

Advantageously, the more active isomer of formula Ia and the intermediate of formula IIa corresponding thereto is isolated.

The compounds are either obtained in the free form, or as a salt thereof. In view of the close relationship between the free compounds and the compounds in the form of their salts, whenever a compound is referred to in this context, a corresponding salt is also intended, provided such is possible or appropriate under the circumstances.

Any resulting free compound can be converted into a corresponding acid addition salt, preferably with the use of a pharmaceutically acceptable acid or anion exchange preparation. The resulting acid-addition salts can be converted into the corresponding free compounds, for example, with the use of one molar equivalent of a base, such as a metal or ammonium hydroxide or a basic salt, e.g. an alkali metal hydroxide or carbonate, or a cation exchange preparation. Compounds of formula I or of formula Ia wherein $COR^2$ and $COR^3$ represent carboxy and of formula II or IIa wherein COR represents carboxy can thus also be converted into the corresponding metal or ammonium salts. These or other salts can also be used for purification of the compounds obtained; the salts are separated and the free compounds are liberated from the salts.

The compounds, including their salts, may also be obtained in the form of their hydrates, or include other solvents used for the crystallization.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg.

EXAMPLE 1

A solution of 15.3 g of 3-bromo-1-ethoxycarbonylmethyl-2,3,4,5-tetrahydro-1H-1-benzazepin-2-one and 30 g of 3-(S)-amino-$\epsilon$-caprolactam [L-(-)-3-aminocaprolactam] in 400 ml of acetonitrile is heated under reflux for 48 hours. The reaction mixture is cooled to room temperature, filtered, and the filtrate is evaporated to dryness. The residue is dissolved in 200 ml methylene chloride, the methylene chloride solution is washed with 2×200 ml of water and then extracted with 2×100 ml of 2N hydrochloric acid. The acidic extract is neutralized to pH 8 by addition of solid potassium carbonate. Extraction with methylene chloride yields 1-ethoxycarbonylmethyl-3-[(2-oxo-(3S)-2,3,4,5,6,7-hexahydro-1H-azepin-3-yl)-amino]-2,3,4,5-tetrahydro-1H-1-benzazepin-2-one as a mixture of diastereoisomers. The crude product is recrystallized from methanol to yield 1-ethoxycarbonylmethyl-3-[(2-oxo-(3S)-2,3,4,5,6,7-hexahydro-1H-azepin-3-yl)-amino]-2,3,4,5-tetrahydro-1H-1-(3S)-benzazepin-2-one, m.p. 148°–150°, the compound of formula IIa wherein COR represents carboxy.

The preparation of 3-bromo-1-ethoxycarbonylmethyl-2,3,4,5-tetrahydro-1H-1-benzazepin-2-one (m.p. 114°–116°) is described in U.S. Pat. No. 4,410,520 (Example 31), issued Oct. 18, 1983.

EXAMPLE 2

A solution of 0.60 g of 1-ethoxycarbonylmethyl-3-[(2-oxo-(3S)-2,3,4,5,6,7-hexahydro-1H-azepin-3-yl)-amino]-2,3,4,5-tetrahydro-1H-1-(3S)-benzazepin-2-one in 20 ml of 6N hydrochloric acid is heated under reflux overnight. The solution is cooled and evaporated to dryness to yield 3-[(5-amino-1-carboxy-(1S)-pentyl)-amino]-1-carboxymethyl-2,3,4,5-tetrahydro-1H-1-(3S)-benzazepin-2-one dihydrochloride, $[\alpha]_D = -136.9°$ (1% in 1N hydrochloric acid), the compound of formula Ia wherein $COR^2$ and $COR^3$ represent carboxy and $R^1$ represents 4-aminobutyl.

The dihydrochloride salt of the product is converted into the free amino acid product by treatment with propylene oxide in ethanol at room temperature overnight.

EXAMPLE 3

3-Bromo-1-ethoxycarbonylmethyl-2,3,4,5-tetrahydro-1H-1-benzazepin-2-one (61.2 g) is added in portions to a suspension of 120 g of L-(−)-3-aminocaprolactam in 1200 ml of acetonitrile. The suspension is heated to reflux and the resulting solution is heated under reflux for 60 hours. The resulting slurry is cooled to room temperature and filtered. The filtrate is evaporated to dryness under reduced pressure at 50°. The residue is taken up in 800 ml of methylene chloride, and the methylene chloride solution is extracted with 2×45 ml of water. The methylene chloride solution is dried over magnesium sulfate and evaporated to dryness. The residue is dissolved in 100 ml of methanol and the mixture is heated to reflux until solution results. Gradual cooling to −10° leads to crystallization of 1-ethoxycarbonylmethyl-3-[(2-oxo-(3S)-hexahydro-1H-azepin-3-yl)-amino]-2,3,4,5-tetrahydro-1H-1-(3S)-benzazepin-2-one hemihydrate, m.p. 145°–147°, $[\alpha]_D = -196.9°$ (1% in chloroform).

The starting material is prepared as follows:

Bromine (327.9 g) is added dropwise while stirring and over a period of one hour, to a solution of 300 g of α-tetralone in 2500 ml of methanol protected from light. The reaction mixture which warms up to about 45° during the addition, is stirred for 30 minutes after completion of the addition of bromine. A solution of 356.5 g of hydroxylamine hydrochloride in 1250 ml of water is added and the reaction mixture is stirred at room temperature for 2.5 days, cooled to 5° and maintained at 5° for one hour. The crystalline product is collected, washed with water, resuspended in 2 liters of water, and filtred off. The product is suspended in 1600 ml of a 3:1 mixture of n-heptane and toluene, and the slurry is stirred for 30 minutes. The crystalline product is filtered off and dried at 35° to give 2-bromo-1-oximino-1,2,3,4-tetrahydronaphthalene, m.p. 125°–131°, which is used directly in the next step.

2-Bromo-1-oximino-1,2,3,4-tetrahydronaphthalene (100 g) is dissolved in 700 ml of toluene at 60°. The immiscible bottom (water) layer is separated. The toluene solution, maintained at 50°–60°, is slowly added while stirring to a mixture of 300 g of polyphosphoric acid and 100 ml of toluene heated to 95°. The reaction mixture is heated under reflux for 75 minutes, and then cooled to 70°. Water (400 ml) is added dropwise over a 30 minute period, maintaining the temperature below 100°. The mixture is then cooled to 5° for 30 minutes. The precipitate is filtered off and washed with water. The product is again suspended in 300 ml of water, and the pH is adjusted to 6 with a 1:1 mixture of concentrated ammonium hydroxide and water. The precipitate is collected, washed with water and slurried in 200 ml of methanol for 20–30 minutes at room temperature. The resulting precipitate is collected, washed with water and dried to give 3-bromo-2,3,4,5-tetrahydro-2-oxo-1H-1-benzazepine, m.p. 172°–174°.

A solution of 20 g of 3-bromo-2,3,4,5-tetrahydro-2-oxo-1H-1-benzazepine in 50 ml of dimethylformamide at 65° is added to a suspension of 114.7 g of potassium carbonate in 200 ml of dimethylformamide at room temperature maintaining the temperature of the reaction mixture below 30°. The reaction mixture is then stirred at room temperature for 90 minutes. A solution of 20.7 g of ethyl bromoacetate in 50 ml of dimethylformamide is added over a period of 30 minutes at room temperature. The reaction mixture is then stirred at 55° for one hour, filtered, the filter cake is washed with 100 ml of dimethylformamide, and the filtrate is evaporated to a small volume (removing about 200 ml of dimethylformamide) at 65° and 40 mm Hg. After cooling to 5°, 250 ml of water is added over a one hour period, maintaining the temperature below 10°, and the suspension is stirred at about 5° for 15 minutes. The solid is filtered off, washed with 200 ml of cyclohexane, and dried at 55° and 40–60 mm for 16 hours to give 3-bromo-1-ethoxycarbonylmethyl-2,3,4,5-tetrahydro-1H-1-benzazepin-2-one.

EXAMPLE 4

A solution of 120 g of 1-ethoxycarbonylmethyl-3-[(2-oxo-(3S)-hexahydro-1H-azepin-3-yl)-amino]-2,3,4,5-tetrahydro-1H-1-(3S)-benzazepin-2-one in 2000 ml of 6N hydrochloric acid is heated over a 30 minute period to 95° and held at this temperature for twenty hours. The reaction mixture is allowed to cool to room temperature. The reaction solution is then evaporated to dryness under vaccuum at 70°. The resulting oil is diluted with 600 ml of water, heated to 70° and treated with charcoal. After stirring at 70° for 30 minutes, the charcoal is filtered off, washed with 100 ml of 6N hydrochloric acid and 200 ml of water. The pH of the combined filtrates is adjusted to pH 5.7–6 with 25% sodium hydroxide, and the mixture is again treated with 12 g of charcoal at 70° for 30 minutes. The charcoal is filtered off and washed with 100 ml of water. The combined filtrates are evaporated to dryness at 70° under vacuum; 300 ml of toluene is added and the resulting mixture is again evaporated to dryness. A slurry of the residue in 2000 ml of a 1:1 mixture of methanol and methylene chloride is stirred for two hours. The mixture is filtred, the filter cake is washed with 500 ml of the 1:1 mixture of methanol and methylene chloride. The combined filtrates are evaporated to dryness. The residue is diluted with water (to a volume of 150 ml) and 800 ml of absolute ethanol is added slowly over a period of 20 minutes with stirring and water cooling to maintain temperature at room temperature. The resulting slurry is cooled to 0° and stirred for four hours. The resulting crystalline product is collected and dried at 60° for twenty hours to yield 3-[(5-amino-1-carboxy-(1S)-pentyl)amino]-1-carboxymethyl-2,3,4,5-tetrahydro-1H-1-(3S)-benzazepin-2-one, $[\alpha]_D^{25} = -172.89°$ (1% in water), melting with decomposition above 210°.

EXAMPLE 5

A mixture of 7.1 g of 1-ethoxycarbonylmethyl-3-[(2-oxo-(3S)-hexahydro-1H-azepin-3-yl)-amino]-2,3,4,5-tetrahydro-1H-1-(3S)-benzazepin-2-one, 20 ml of Amberlite ®  IR-120 (H+ form) ion exchange resin, and 40 ml of water is heated at reflux temperature for 18 hours. The reaction mixture is cooled and filtered. A mixture of the filtered off resin and 35 ml of 10% aqueous ammonium hydroxide is stirred at room temperature for 1 hour. The reaction mixture is filtered. Similar treatment of the resin with 35 ml of 10% aqueous ammonium hydroxide is repeated twice; the three filtrates are evaporated to dryness to yield 3-[(5-amino-1-carboxy-(1S)-pentyl)-amino]-1-carboxymethyl-2,3,4,5-tetrahydro-1H-1-(3S)-benzazepin-2-one, identical to the compound of Example 4.

What is claimed is:

1. A process for the preparation of a compound of the formula

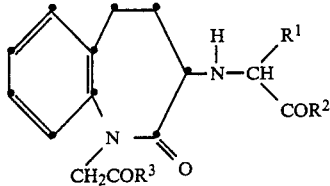

wherein R¹ represents 4-aminobutyl, COR² and COR³ represent carboxy; or a pharmaceutically acceptable salt thereof; which comprises ring opening the monocyclic lactam in a compound of the formula

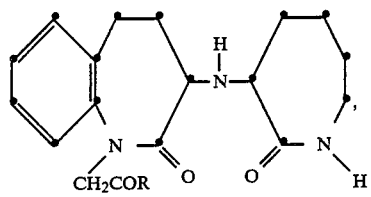

wherein COR represents carboxy or esterified carboxy, and hydrolysis of the esterified carboxy group when COR represents esterified carboxy; esterified carboxy comprising lower alkoxycarbonyl, benzyloxycarbonyl, benzyloxycarbonyl substituted in the phenyl ring by lower alkyl, halogen or lower alkoxy, or pyridylmethoxycarbonyl.

2. A process according to claim 1 wherein COR in a compound of formula II represents carboxy or lower alkoxycarbonyl.

3. A process according to claim 1 carried out under acidic conditions.

4. A process according to claim 1 carried out with a mineral acid, a lower alkylsulfonic acid or an acidic ion exchange resin.

5. A process according to claim 1 carried out with a mineral acid.

6. A process according to claim 1 carried out with an acidic ion exchange resin.

7. A process according to claim 1 for the preparation of the compound of the formula Ia

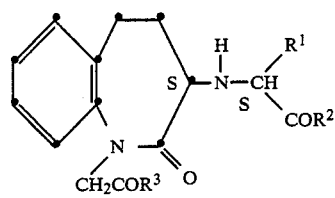

wherein R¹ represents 4-aminobutyl, COR² and COR³ represent carboxy; or a pharmaceutically acceptable salt thereof; which comprises ring opening the monocyclic lactam in a compound of formula IIa

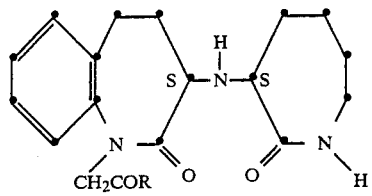

wherein COR represents carboxy or esterified carboxy, as defined in claim 1 and hydrolysis of the esterified carboxy group when COR represents esterified carboxy.

8. A process according to claim 7 wherein COR in a compound of formula IIa represents carboxy or lower alkoxycarbonyl.

9. A process, according to claim 1 for the preparation of 3-[(5-amino-1-carboxy-(1S)-pentyl)amino]-1-carboxymethyl-2,3,4,5-tetrahydro-1H-1-(3S)-benzazepin-2-one or a pharmaceutically acceptable salt thereof, which comprises reacting 1-ethoxycarbonylmethyl-3-[(2-oxo-(3S)-hexahydro-1H-azepin-3-yl)-amino]-2,3,4,5-tetrahydro-1H-1-(3S)-benzazepin-2-one with a strong mineral acid.

10. A process according to claim 9 carried out with aqueous hydrochloric acid.

11. A process according to claim 9 carried out with aqueous hydrochloric acid at elevated temperature.

12. A compound of the formula

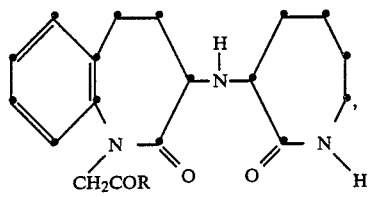

wherein COR represents carboxy; or COR represents esterified carboxy comprising lower alkoxycarbonyl, benzyloxycarbonyl, benzyloxycarbonyl substituted in the phenyl ring by lower alkyl, halogen or lower alkoxy, or pyridylmethoxycarbonyl; or an acceptable salt thereof.

13. A compound according to claim 12 wherein COR represents carboxy or lower alkoxycarbonyl; or an acceptable salt thereof.

14. A compound according to claim 12 of the formula

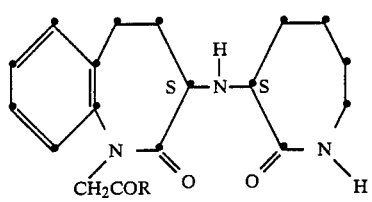

wherein COR represents carboxy or esterified carboxy; as defined in claim 12 or an acceptable salt thereof.

15. A compound according to claim 14 wherein COR represents carboxy or lower alkoxycarbonyl; or an acceptable salt thereof.

16. A compound according to claim 15, wherein COR in formula IIa is ethoxycarbonyl, being 1-ethoxycarbonylmethyl-3-[(2-oxo-(3S)-hexahydro-1H-azepin-3-yl)-amino]-2,3,4,5-tetrahydro-1H-1-(3S)-benzazepin-2-one; or an acid addition salt thereof.

* * * * *